United States Patent
Magara et al.

(10) Patent No.: US 11,337,797 B2
(45) Date of Patent: May 24, 2022

(54) CAM ACTUATED BASE FOLDING MECHANISM

(71) Applicant: Alcon Inc., Fribourg (CH)

(72) Inventors: Len Takudzwa Magara, Pretoria (ZA); Douglas Brent Wensrich, Bedford, TX (US); Yinghui Wu, Cedar Hill, TX (US); Rudolph F. Zacher, Trabuco Canyon, CA (US); Todd Taber, Keller, TX (US)

(73) Assignee: Alcon Inc., Fribourg (CH)

( * ) Notice: Subject to any disclaimer, the term of this patent is extended or adjusted under 35 U.S.C. 154(b) by 420 days.

(21) Appl. No.: 16/533,385

(22) Filed: Aug. 6, 2019

(65) Prior Publication Data

US 2020/0197160 A1 Jun. 25, 2020

Related U.S. Application Data

(60) Provisional application No. 62/781,727, filed on Dec. 19, 2018.

(51) Int. Cl.
*A61F 2/16* (2006.01)
*A61F 9/00* (2006.01)

(52) U.S. Cl.
CPC ............ *A61F 2/167* (2013.01); *A61F 2/1678* (2013.01); *A61F 9/0017* (2013.01)

(58) Field of Classification Search
CPC ...... A61F 2/167; A61F 2/1678; A61F 2/1672; A61F 2/1675; A61F 2/1691; A61F 9/0017; A61F 9/0008; A61F 9/0026; A61F 9/0061
See application file for complete search history.

(56) References Cited

U.S. PATENT DOCUMENTS

| | | | |
|---|---|---|---|
| 6,497,708 B1 * | 12/2002 | Cumming | A61F 2/1664 606/107 |
| 8,460,375 B2 * | 6/2013 | Tran | A61F 2/1678 623/6.12 |
| 9,364,316 B1 | 6/2016 | Kahook et al. | |
| 2005/0149056 A1 | 7/2005 | Rathert | |
| 2009/0204122 A1 * | 8/2009 | Ichinohe | A61F 2/167 606/107 |
| 2016/0270907 A1 * | 9/2016 | Attinger | A61F 2/1672 |
| 2017/0319332 A1 | 11/2017 | Kahook et al. | |

FOREIGN PATENT DOCUMENTS

EP      1857074 A1      11/2007

* cited by examiner

*Primary Examiner* — Tan-Uyen T Ho
*Assistant Examiner* — Chima U Igboko

(57) ABSTRACT

Systems, methods, and devices for inserting an intraocular lens (IOL) assembly into an eye may be provided. A device for delivery of the IOL into the eye may include a nozzle; a bay adjacent to the nozzle, wherein the bay is configured to contain the lens component and comprises a recess in a shape of a haptic extension; and a cam-actuated mechanism comprising a slider configured to move in a direction toward the nozzle; a side arm moveably disposed within the bay, wherein the side arm is positioned at an end of the slider, the end of the slider comprising a groove aligned with the side arm, wherein the groove extends from an outer edge of the slider into an interior portion of the slider, wherein the groove is angled to receive the side arm as the slider moves.

6 Claims, 13 Drawing Sheets

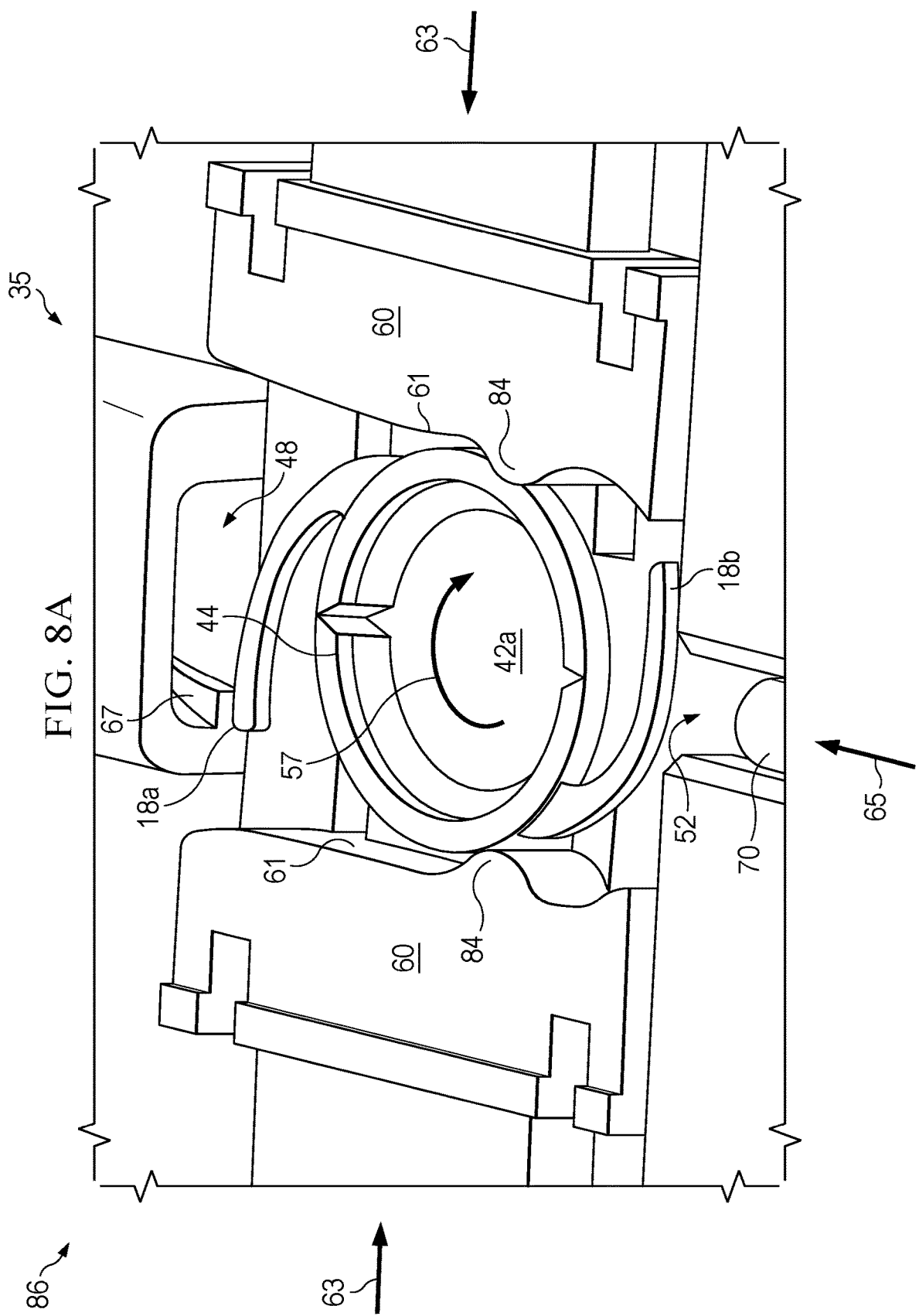

CAM ACTUATED BASE FOLDING MECHANISM

TECHNICAL FIELD

The present disclosure generally relates to eye surgery and, more particularly, embodiments may generally relate to systems, methods, and devices for folding or rolling an intraocular lens (IOL) for delivery into a patient's eye.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded lens with an intraocular lens (IOL). An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate bay may be loaded into the insertion tool. The plunger may engage the IOL to advance the IOL from the bay, through the nozzle, and into the eye. The bay (or insertion tool) may include a folding chamber configured to cause the IOL to fold, for example, when the IOL advances through the folding chamber. In some instances, a separate action may cause folding of the IOL.

Delivery of the IOL from the insertion tool can be a multi-step process. For example, the delivery may include two stages, which may be referred to as an advancing stage and a delivery stage. In the advancing stage, the IOL can be advanced from a storage position in the bay to a dwell position. The IOL may be pre-folded or may be folded when advanced from the storage position to the dwell position. At the dwell position, advancement of the IOL may be halted. With the nozzle positioned in the eye, the IOL may then be further advanced from the dwell position, in the delivery stage, which may include advancing the IOL through the nozzle and into the eye.

SUMMARY

In an exemplary embodiment, the present disclosure provides an apparatus for delivery of a lens component into an eye. The apparatus includes a nozzle; a bay adjacent to the nozzle, wherein the bay is configured to contain the lens component and comprises a recess in a shape of a haptic extension; and a cam-actuated mechanism comprising a slider configured to move in a direction toward the nozzle; a side arm moveably disposed within the bay, wherein the side arm is positioned at an end of the slider, the end of the slider comprising a groove aligned with the side arm, wherein the groove extends from an outer edge of the slider into an interior portion of the slider, wherein the groove is angled to receive the side arm as the slider moves.

In another exemplary embodiment, the present disclosure provides an apparatus for delivery of a lens component into an eye. The apparatus includes a nozzle; a bay adjacent to the nozzle, wherein the bay is configured to contain the lens component and comprises a recess in a shape of a haptic extension; and a cam-actuated mechanism comprising a slider configured to move in a direction toward the nozzle; a first side arm moveably disposed within the bay; a second side arm moveably disposed within the bay, wherein the first side arm is positioned opposite to the second side arm, wherein the side arms are positioned at an end of the slider, the end of the slider comprising grooves aligned with the side arms, wherein the grooves extends from outer edges of the slider into an interior portion of the slider, wherein the grooves are angled to receive the side arms as the slider moves.

In an exemplary embodiment, the present disclosure provides a method for delivery of a lens component into an eye. The method includes inserting a nozzle of an insertion tool into the eye, wherein the insertion tool further comprises a bay adjacent to the nozzle, wherein the bay contains the lens component and comprises a haptic recess in a shape of a haptic extension; and a cam-actuated mechanism comprising a slider configured to move in a direction toward the nozzle; a side arm moveably disposed within the bay, wherein the side arm is positioned at an end of the slider, the end of the slider comprising a groove aligned with the side arm, wherein the groove extends from an outer edge of the slider into an interior portion of the slider, wherein the groove is angled to receive the side arm as the slider moves. The method further includes moving the slider in a direction toward the nozzle; receiving the side arm within the groove; compressing the lens component in the bay with the side arm; and moving the lens component from the bay, through the nozzle and into the eye.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIG. 8A. illustrates dual side arms in accordance with embodiments of the present disclosure;

DETAILED DESCRIPTION

Figure 1:
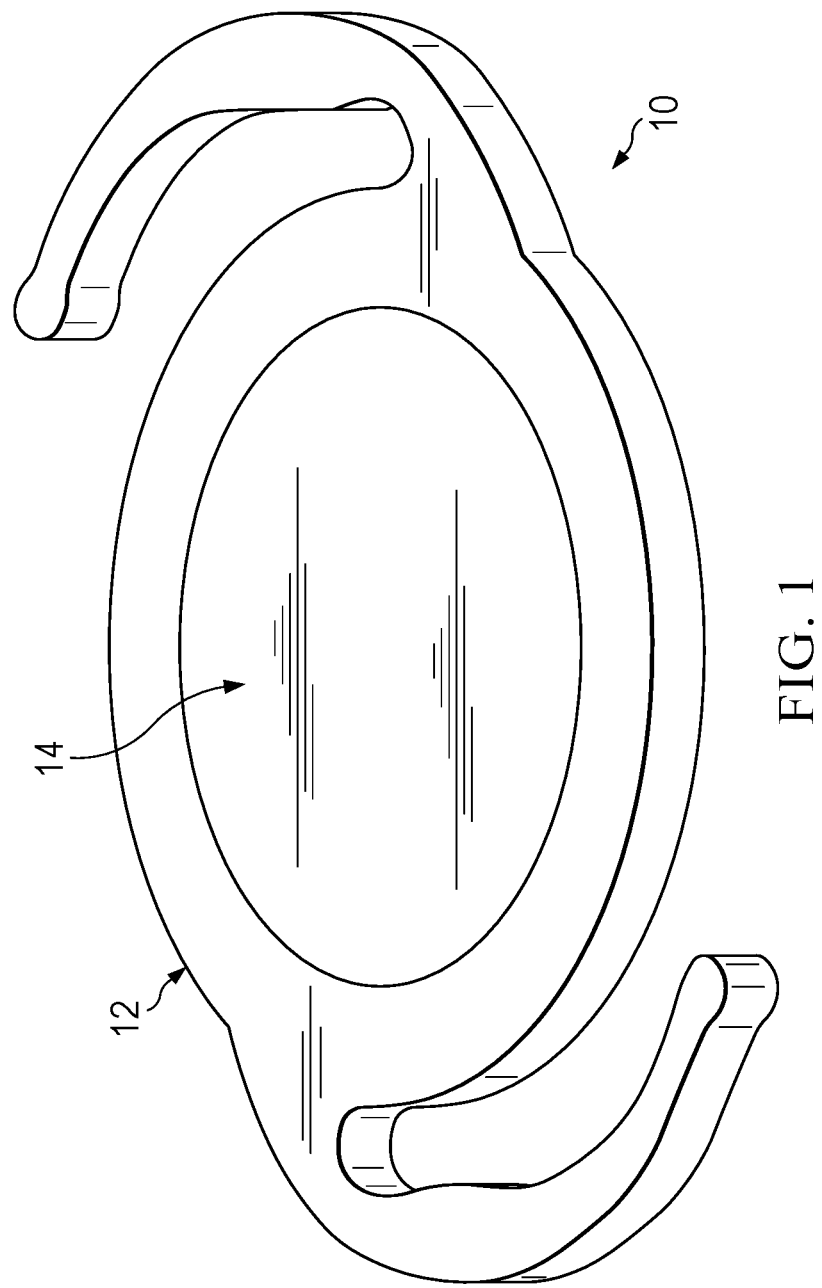
FIG. 1 illustrates a modular IOL with a lens portion positioned in a base portion in accordance with embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments may generally relate to eye surgery. More particularly, embodiments may generally relate to systems, methods, and devices for folding or rolling an intraocular lens (IOL) for delivery into a patient's eye.

Any suitable IOL may be used, including, but not limited to, IOLs that include a lens portion and haptic extensions. The haptic extensions may be side struts (or other suitable extensions) that extend from the lens portion to hold the lens portion in place when implanted in the eye. In at least one embodiment, the IOL may be modular. Embodiments of a modular IOL may include a base portion and a lens portion. The base portion may include the haptic extensions. The lens portion may be coupled to the base portion to form the modular IOL.

In certain embodiments, the base portion may be a hollow ring with two protruding haptic arms, which means a center of mass of the base portion is more complex than typical one-piece IOLs. A central axis of the base portion can change when external forces are applied, which increases the difficulty in folding it. This complex geometry requires evenly distributed force application on an optic centroid of the base portion as well as symmetric opposing forces to fold the haptics. Challenges associated with the base portion may include the base portion not retaining its shape/structure as it is advanced, a trailing haptic not folding correctly, as well as the base portion rolling about an axis perpendicular to the optic centroid.

Embodiments of the present disclosure address these challenges by including an insertion tool that compresses (e.g., folds or rolls) the base portion to keep the haptics (or haptic extensions) against the ring's outer edge. The base portion may be positioned in a bay of the insertion tool. The ring may be elongated due to an application of a uniform compressive force across an entire length of the base portion, to allow for a more constant center of mass. A side arm of the insertion tool, which creates this compressive force, may contact the base portion with a wall that may be slanted at an angle ranging, for example, from 1°-5° (e.g., 2°). This angle may allow for more compression at a trailing haptic extension than at a leading haptic extension. This may allow the trailing haptic extension to fold more consistently. Once the folding is complete, a plunger can be utilized to advance the folded base portion in its compressed state until the base portion is delivered in a patient's eye via a nozzle of the insertion tool.

The insertion tool may include a cam-actuated folding mechanism to fold the IOL. The cam-actuated folding mechanism may be actuated as part of advancing the IOL to the dwell location with a plunger. The mechanism includes the side arm that compresses the IOL upon depression of the plunger of the insertion tool. The side arm and an interior wall of the bay may include surface topography configured to fold and compress the IOL (e.g., according to ISO 11979-3 standard) for delivery into a patient's eye. The cam-actuated folding mechanism may also include a slider that moves axially (e.g., via depression of the plunger) causing the side arm to move in a lateral or inward direction (e.g., toward the insertion tool). The cam-actuated folding mechanism may allow for a controlled and consistent force application and may improve speed control during compression of the base portion.

Some embodiments may include a side arm that includes a floor, wall, or contact side that may be completely flat (e.g., no bumps) to reduce pinch points that may cause the base portion to become stuck during advancement or folding. The side arm may be thickened to provide a more uniform force distribution during the folding action. Also, the side arm may be configured to compress a trailing haptic extension of the base portion more than a leading haptic extension of the base portion. Embodiments may also include a cover to the bay that may include longer and stronger snaps and may be constrained at three rather than two points for improved stability.

FIG. 1 illustrates an embodiment of a modular IOL 10. The modular IOL 10 may be any suitable modular interocular lens. As illustrated, the modular IOL 10 may include a base portion 12 and a lens portion 14. In the illustrated embodiment, the lens portion 14 is positioned in the base portion 12. In operation, the modular IOL 10 can allow for the lens portion 14 to be modified or adjusted while leaving the base portion 12 in place, either intra-operatively or post-operatively. By way of example, the modular IOL 10 may be implanted into an eye. After implantation, the lens portion 14 may be modified, adjusted, and/or replaced while leaving the base portion 12 positioned in the eye. In at least one embodiment, the modular IOL 10 may be assembled in the eye. For example, the base portion 12 may first be implanted in the eye. The lens portion 14 may then be delivered into the eye and attached to the base portion 12.

Figure 2:
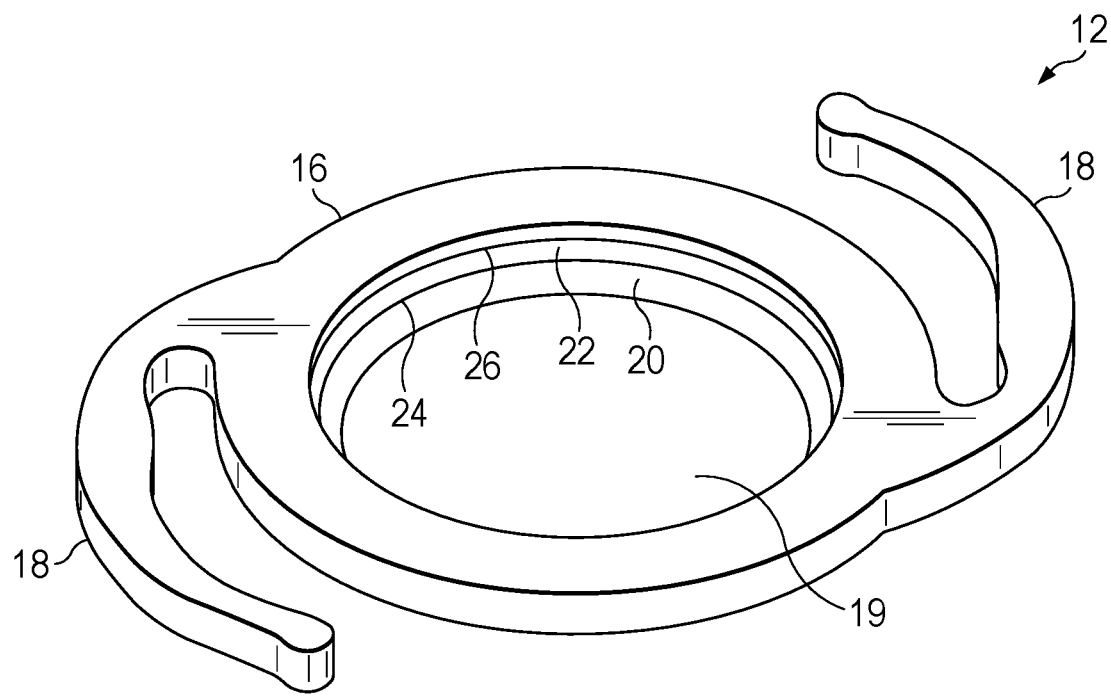
FIG. 2 illustrates a base portion of a modular IOL in accordance with embodiments of the present disclosure.

FIG. 2 illustrates the base portion 12 of the modular IOL 10 of FIG. 1 in accordance with embodiments of the present disclosure. In the illustrated embodiment, the base portion 12 includes a base 16 and haptic extensions 18. The haptic extensions 18 may be side struts (or other suitable extensions) extending from the base 16 that may stabilize the base portion 12 when it may be disposed within the patient's eye. In the illustrated embodiment, the base 16 may define a hole 19, which may be centrally located in the base 16 as shown on FIG. 2. While the hole 19 is shown as a through hole extending through the base 16, embodiments also contemplate hole 19 being a blind hole that does not extend through the base 16. For example, the base 16 may be a solid disc with the hole 19 being a blind hold that does not extend through the base 16, rather than an annular ring with the hole 19 extending through the base 16. Hole 19 may be defined by inner perimeter surface 20 of the base 16. In at least one embodiment, a recessed groove 22 is formed in inner perimeter surface 20. Recessed groove 22 may include a lower rim 24 and an upper rim 26. The upper rim 26 may have an insider diameter that is the same as or greater than the outside diameter of the lens portion 14 (excluding tabs 30 shown on FIG. 3) such that the lens portion 14 can rest inside the hole 19 of the base 16. All or a portion of the lower rim 24 can have an inside diameter that is less than the outside diameter of the lens portion 14 (excluding tabs 30 shown on FIG. 3) such that the lower rim 24 can act as a ledge or backstop for the lens portion 14 when placed in the hole 19 of the base 16. The base portion 12 may be unitary or may be formed from component parts that are combined or attached in any suitable manner.

Figure 3:
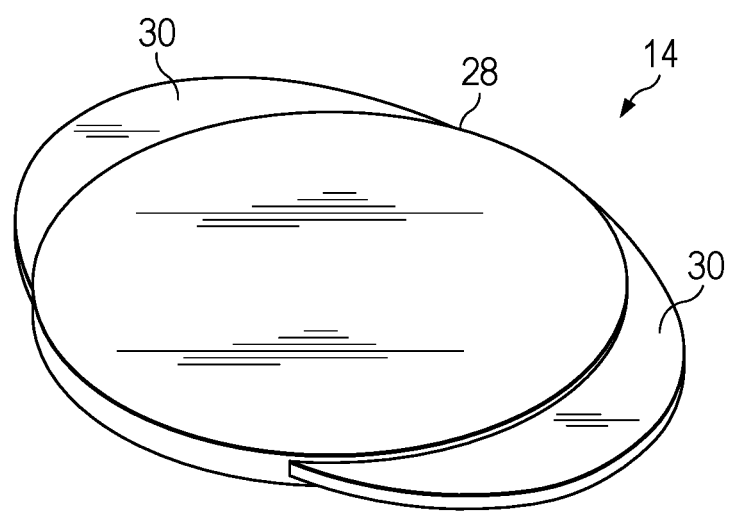
FIG. 3 illustrates a lens portion of a modular IOL in accordance with embodiments of the present disclosure.

With reference to FIG. 3, the lens portion 14 of the modular IOL 10 of FIG. 1 is illustrated in accordance with embodiments of the present disclosure. In the illustrated embodiments, the lens portion 14 includes an optic portion 28 and one or more tabs 30. While FIG. 3 illustrates two of the tabs 30, embodiments may include only one of the tabs 30 or alternatively three, four, or more of the tabs 30. In addition, the tabs 30 on the lens portion 14 may be the same or different from one another. The tabs 30 are shown as being fixed to the optic portion 28; however, it should be understood that one or more of the tabs 30 may be actuated to move from a compressed position for delivery into the hole 19 of the base 16 (e.g., shown on FIG. 2) to an uncompressed extended position for deployment into the recessed groove 22 of the base 16 (e.g., shown on FIG. 2), thus forming an interlocking connection between the base portion 12 and the lens portion 14. The outside curvature of the tabs 30 may have a radius conforming to the inside radius of the recessed groove 22. This arrangement should limit relative movement between the base portion 12 and the lens portion 14 once connected. In embodiments, a suitable optic portion 28 may be in a shape similar to that of a natural lens within the eye and made from a suitable material such as silicone, acrylic, and/or combinations thereof. While the optic portion 28 is shown as being circular, the optic portion 28 may be any suitable shape, such as oval or ellipsoidal, for example, with the tabs 30 positioned adjacent the long axis. This arrangement would thus define a gap between the edge of the optic portion 28 along its short axis and the inner perimeter surface 20 in the base 16. The gap may enable access for a probe or similar device to pry apart the lens portion 14 from the base portion 12 if separation were needed.

Figure 4:
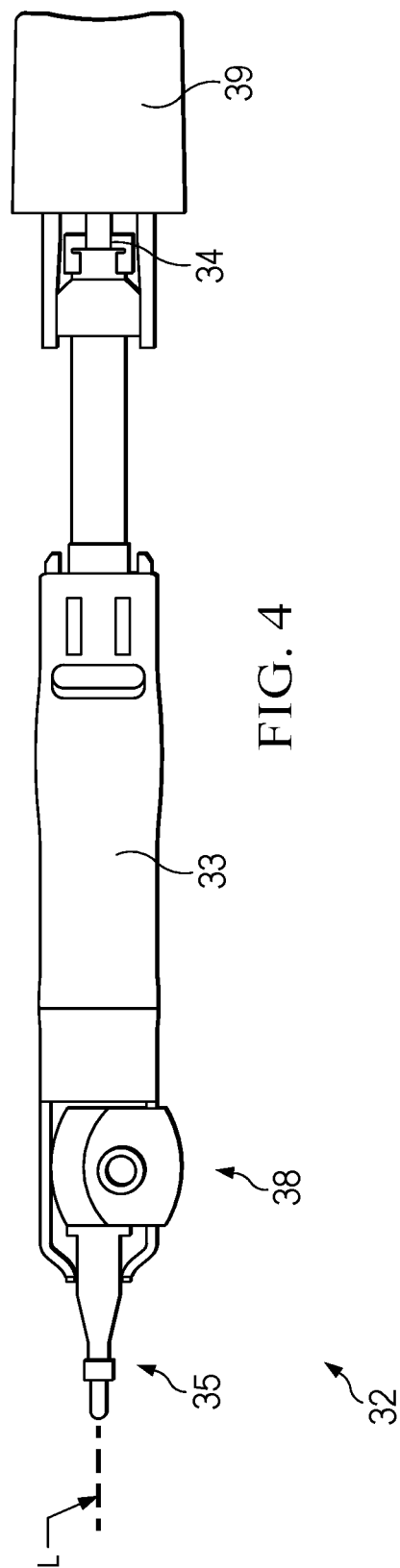
FIG. 4 is a top view of an insertion tool in accordance with embodiments of the present disclosure.

FIG. 4 illustrates a top view of an insertion tool 32 in accordance with exemplary embodiments. The insertion tool 32 may include a housing 33, a plunger 34 at least partially disposed axially within the housing 33, and a nozzle 35. The plunger 34 is slidably disposed within the housing 33 and may move axially along a longitudinal axis of the housing 33. A plunger head 39 may be coupled to the plunger 34 and may be positioned exterior to the housing 33. The nozzle 35 may be disposed on end of the insertion tool 32 that is opposite to the plunger head 39, as shown. In other words, the plunger 34 and the plunger head 39 may extend from a first end of the housing 33, and the nozzle 35 may extend from a second opposite end of the housing 33, as shown. A user may depress the plunger head 39 to move the plunger 34 axially (toward the nozzle 35) within the housing 33. The housing 33 may be configured to receive the nozzle 35. In some embodiments, the nozzle 35 may be attachable the housing 33 so that the nozzle 35 can be coupled and decoupled from the housing 33.

Figure 5A:
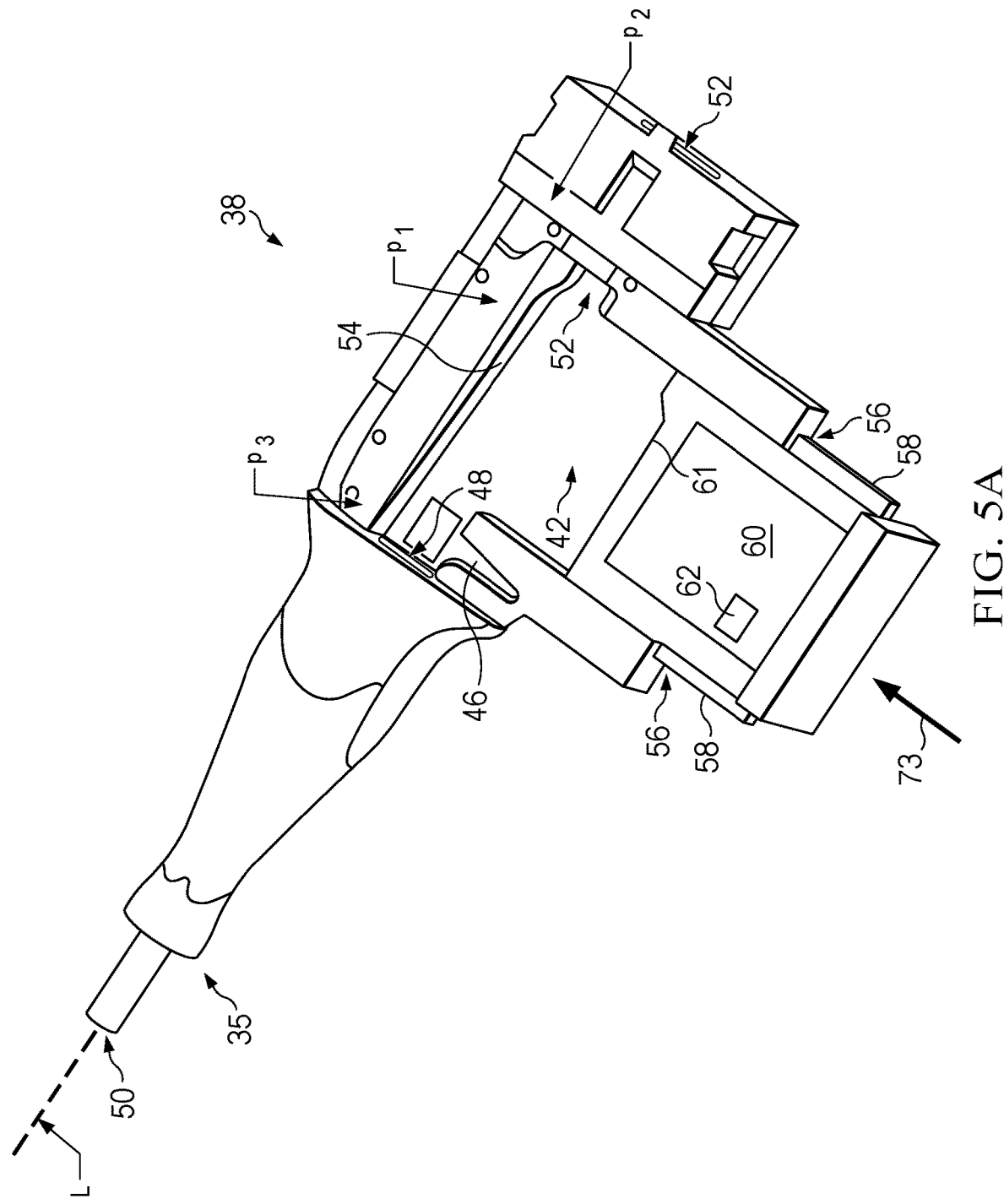
FIGS. 5A-5C are perspective views of a front portion of an insertion tool in accordance with embodiments of the present disclosure.
Figure 5B:
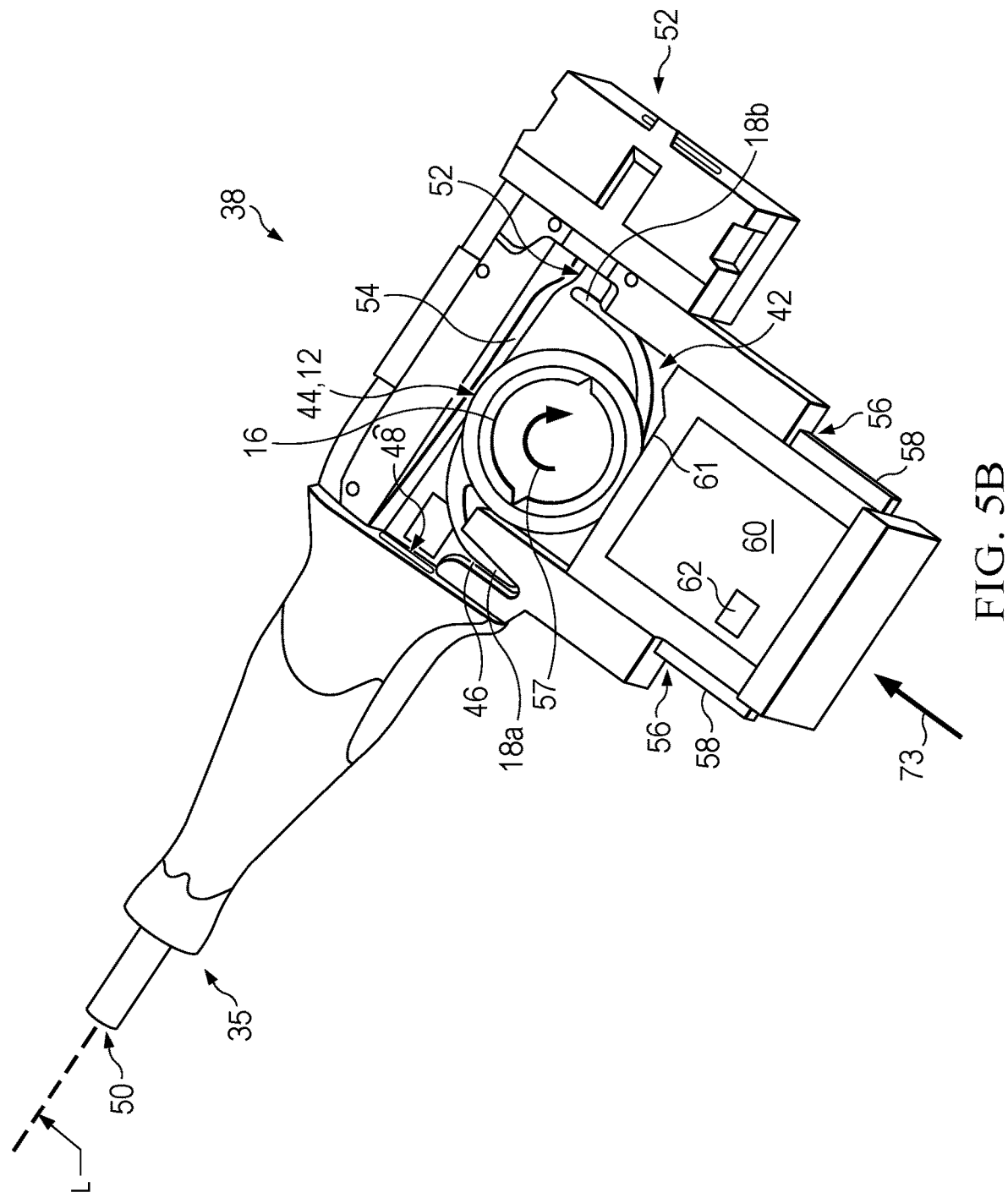
Figure 5C:
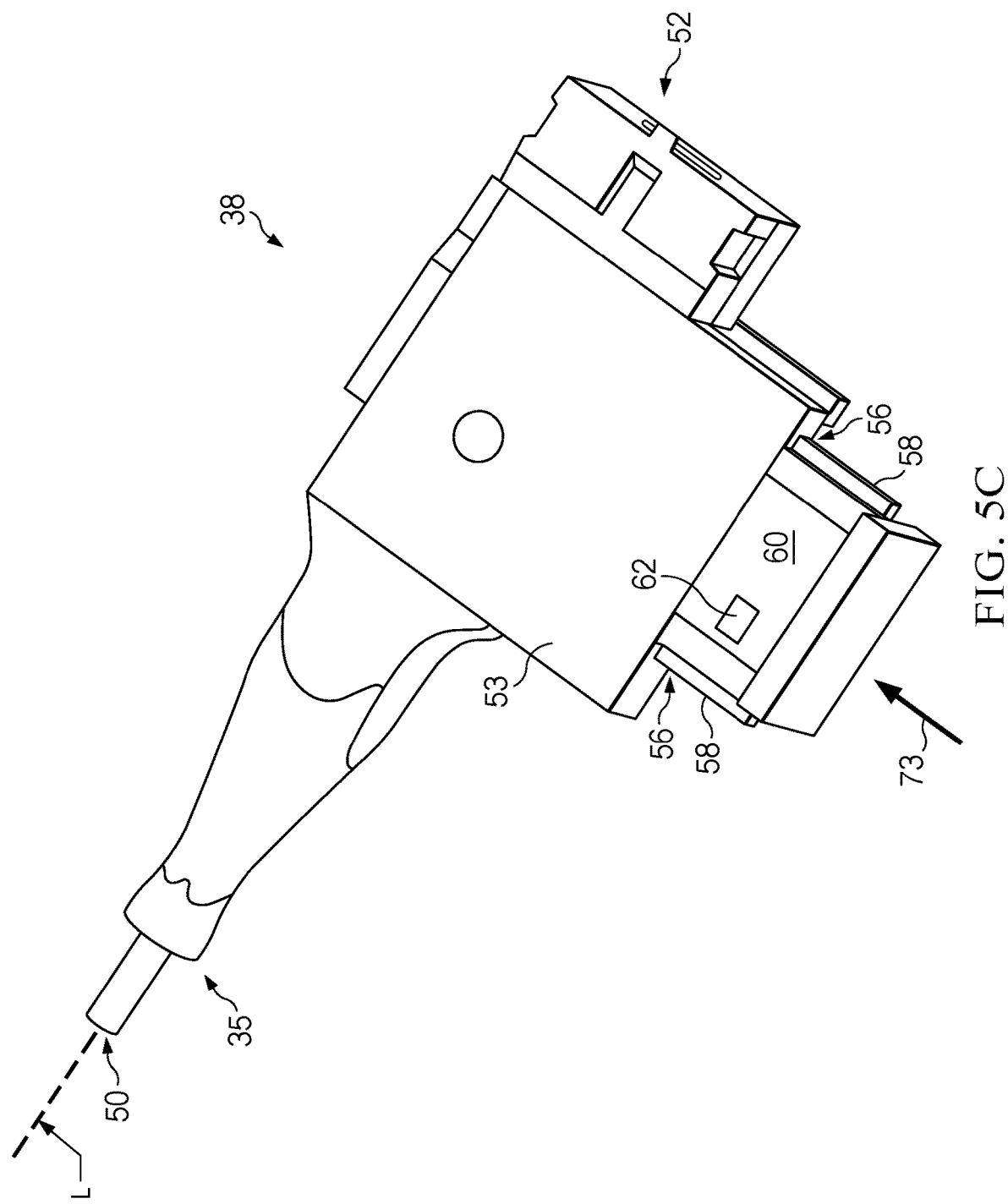

FIGS. 5A-5C illustrate views of a front portion 38 of an insertion tool that is similar to the insertion tool 32 of FIG. 4 in accordance with ex. The front portion 38 may include a bay 42. The bay 42 may be a compartment that holds a lens component 44. The bay 42 may also be filled with a viscoelastic lubricant. The lens component 44 may include at least one component of the modular IOL 10 shown on FIG. 2, such as the base portion 12 or the lens portion 14. The lens component 44 may be positioned within the bay 42 of the insertion tool 32, as shown on FIGS. 5B and 5C.

The bay 42 may include a haptic recess 46 (e.g., an elongated recess conformed to a shape of a haptic extension) for holding and stabilizing a leading haptic extension 18a. The haptic recess 46 may be positioned adjacent to intake 48 of the nozzle 35. An intake 48 is in fluid communication with an aperture 50 (exit) of the nozzle 35. The lens component 44 (e.g., folded) may be delivered into a patient's eye from the bay 42 via the intake 48 and out the aperture 50. The bay 42 may also include a channel 52 to receive the plunger 34 or a shaft that receives an axial force from the plunger 34. An axial push of the plunger 34 allows compression and transfer of the lens component 44 from the bay 42 via the intake 48 and out the aperture 50 into a patient's eye. That is, actuation of the plunger 34 causes the plunger 34 (or a shaft that receives the axial force from the plunger) to pass through the channel 52 and contact and push the lens component 44 (in a compressed state) that is positioned in the bay 42, through the intake 48, through the nozzle 35 and out the aperture 50 and into the patient's eye.

The bay 42 may also include an interior wall 54 configured to compress the lens component 44. The interior wall 54 may extend from the channel 52 to the intake 48 of the nozzle 35 and may extend in a direction along a longitudinal axis L of the front portion 38. The interior wall 54 may slant (e.g., an angle ranging from 1°-5° (e.g., 2°)) or curve to assist with folding the lens component 44 in the bay 42.

Additionally, a cover 53 may be removably attached to the bay 42. The cover 53 may removably attach to at least 3 portions (e.g., p$_1$, p$_2$, p$_3$, shown on FIG. 5A) of the bay 42, as shown. The cover 53 may attach to the bay 42 via a friction fit or (e.g., fitted into place via tabs and/or recesses). The bay 42 may also include rails 56 to receive portions 58 of a side arm 60. The cover 53 may be removed to allow placement of the lens component 44 into the bay 42 and to also allow the viscoelastic lubricant to be placed in the bay 42. The cover 53 may be repositioned on the bay 42 to secure the lens component 44 and the viscoelastic lubricant in the bay 42.

The side arm 60 may be a rigid member positioned opposite to the interior wall 54. The side arm 60 may be configured to move toward the interior wall 54 along the rails 56 (see arrow 73), as the plunger 34 is depressed, and compress the lens component 44 such that the lens component 44 rotates (indicated by arrow 57). The lens component 44 may be compressed into an ellipse or hemisphere type shape, wherein a major axis of the ellipse generally extends in a direction of travel of the plunger 34 and the lens component 44 (e.g., in a direction along a longitudinal axis, L, of the front portion 38 and the nozzle 35).

The side arm 60 may include a wall 61 including a slant or curve similar to that of the interior wall 54 to also assist with folding the lens component 44 in the bay 42. That is, the slant facilitates tucking of a trailing haptic extension 18b.

The lens component 44 is compressed between the wall 61 of the side arm 60 and the interior wall 54 of the bay 42.

Figure 6:
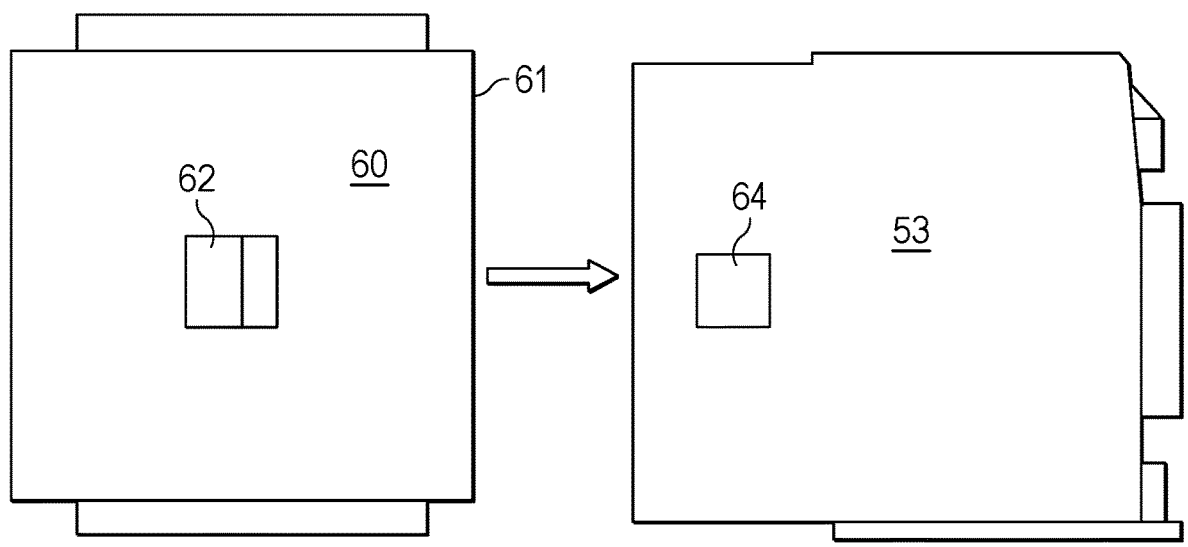
FIG. 6 illustrates a side arm and a cover of an insertion tool in accordance with embodiments of the present disclosure.

As shown on FIG. 6, the side arm 60 may include a raised portion 62 (e.g., a button) including a ramp configured to slide along an interior portion of the cover 53 (see arrow) and extend into an aperture 64 of the cover 53, as the side arm 60 slides toward the interior wall 54, upon depression of the plunger 34. The positioning of the raised portion 62 within the aperture 64 locks the side arm 60 in place thereby maintaining the lens component 44 in the compressed or elliptical shape.

Figure 7A:
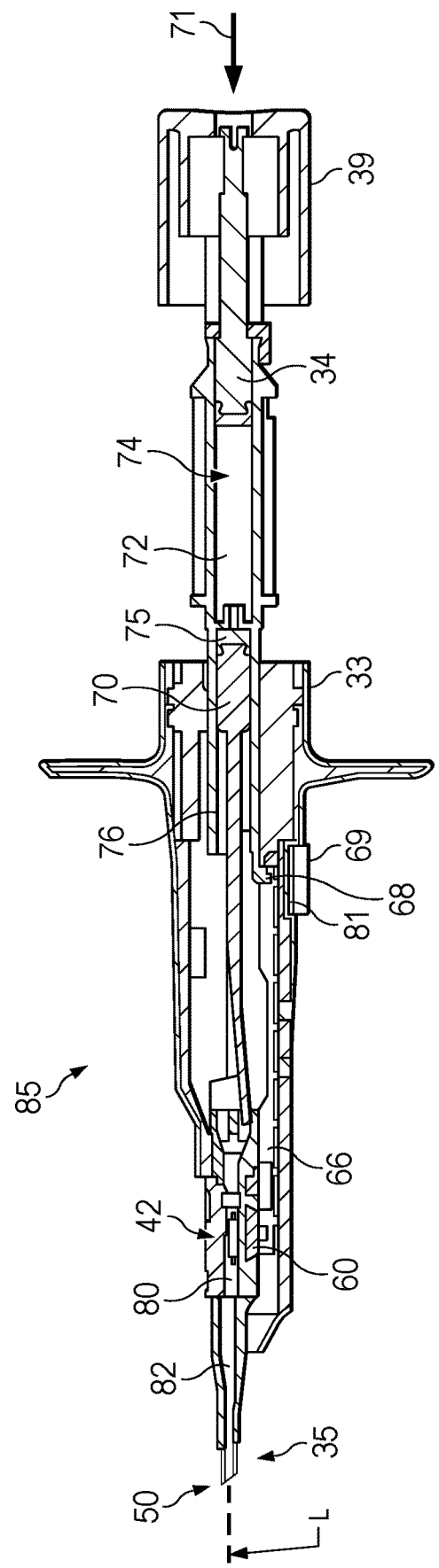
FIG. 7A is a cross-section of a top view of an insertion tool including a slider and a side arm in accordance with embodiments of the present disclosure.

FIG. 7A is a cross sectional view of the top view (entire length) of an insertion tool 85 that is similar to the insertional tool 32 of FIG. 4. As shown on FIG. 7A, the insertion tool 85 further includes a slider 66 that may be a rigid structure (e.g., an elongated member). The side arm 60 may be positioned at a distal end of the slider 66. The slider 66 may be coupled to a member 68 that extends from a plunger assembly 37 of the insertion tool 85. The plunger assembly 37 may be movably disposed within the insertion tool 85 and may include a first cylinder 74 in fluid communication with a second cylinder 76 via an orifice 75. The plunger assembly 37 may further include a shaft 70 movably disposed within the second cylinder that is downstream to the first cylinder 74. For example, the plunger 34 may be depressed in a direction toward the nozzle 35 (see arrow 71) to force a hydraulic fluid 72 from the first cylinder 74 into the second cylinder 76 via the orifice 75, as shown. This causes the hydraulic fluid 72 to propel the shaft 70 (the shaft 70 may be positioned within the second cylinder 76) toward the nozzle 35 (and through the bay 42 to contact and push the lens component 44 through the nozzle 35). The depression of the plunger 34 may also cause the plunger assembly 37 (unlocked) to move axially (e.g., forward).

A tab 69 may be a locking mechanism that can be pulled away from the plunger assembly 37. The tab 69 may be slidably positioned within a recess 81 of the housing 33. When in an unlocked position (as shown), the tab 69 is pulled away (see arrow) from the member 68 thereby allowing axial movement of the plunger assembly 37 when the plunger 34 is depressed. In a locked position, the tab 69 prevents axial movement of the plunger assembly 37 by abutting the member 68.

The tab 69 may move in a direction orthogonal to the longitudinal axis L. The tab 69 may be confined to the recess 81 by edges or grooves within the recess 81. In certain embodiments, the tab 69 cannot be pulled out completely away from the insertion tool 32. The lack of a completely removable lock provides a benefit of one less part to discard in a sterile field during a procedure.

Figure 7B:
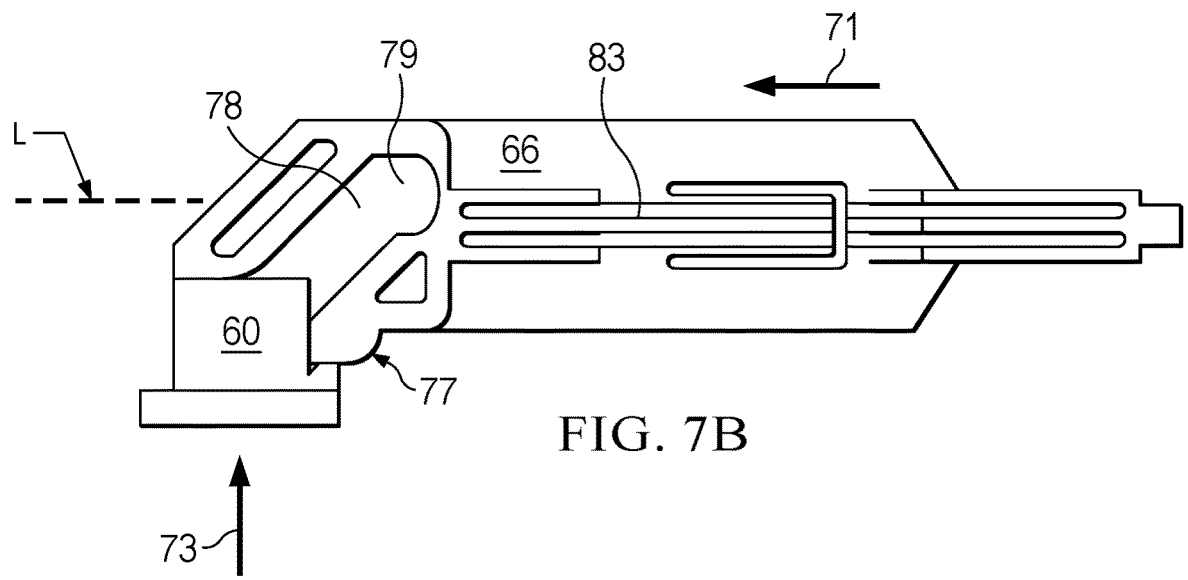
FIG. 7B is a top view of the slider and the side arm of FIG. 7A in accordance with embodiments of the present disclosure.
Figure 7C:
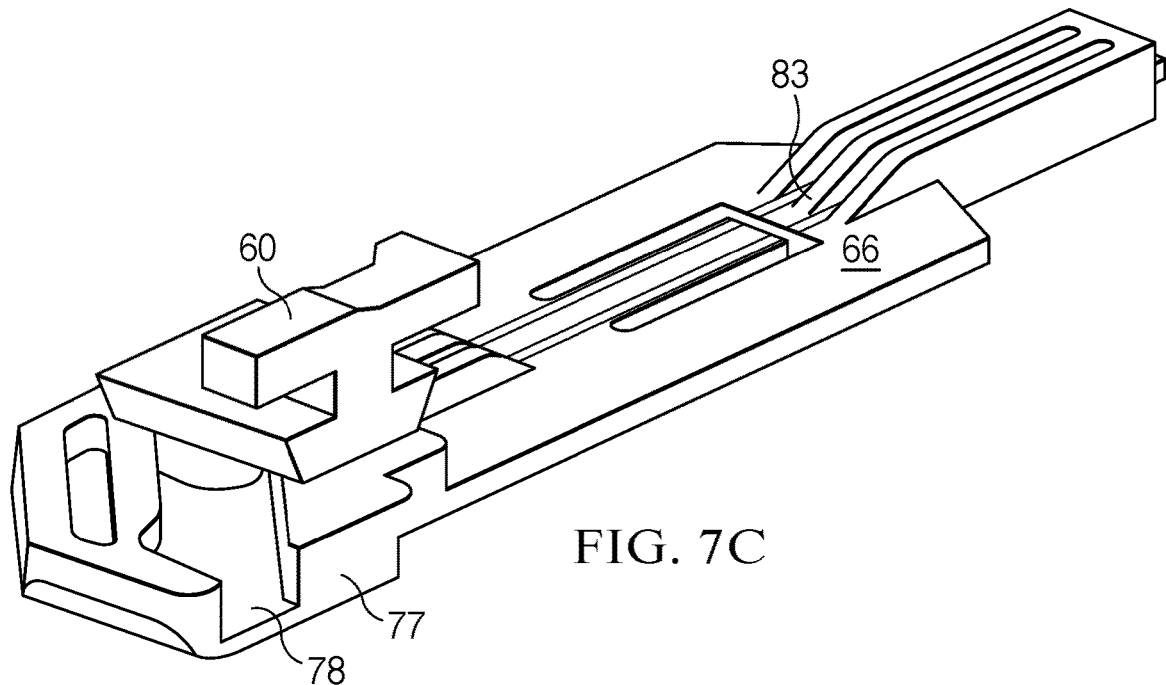
FIG. 7C is a side perspective view of the slider of FIG. 7B in accordance with embodiments of the present disclosure.

FIGS. 7B and 7C illustrate a top view and a side perspective view, respectively, of the slider 66 and the side arm 60 in accordance with exemplary embodiments. When unlocked, the slider 66 may move axially (see arrow 71) upon depression of the plunger 34 (and the shaft 70). The slider 66 may include tracks 83 that contact and correspond with projections (or rails) of an interior portion of the housing 33 to guide axial movement of the slider 66 within the tracks 83. The tracks 83 may extend in a direction that is perpendicular to the rails 56.

As the plunger 34 is depressed, the shaft 70 and the slider 66 move axially (toward the nozzle 35). The slider 66 contacts the side arm 60, and the side arm 60 moves along a groove 78 of the slider 66. The groove 78 may be positioned at a distal end of the slider 66, as shown. The side arm 60 slides from an outer edge 77 of the slider 66 inward (e.g., toward an inner portion 79 of the slider 66 and/or toward the interior wall 54 of the bay 42), thereby compressing the lens component 44 between the wall 61 of the side arm 60 and the interior wall 54 of the bay 42.

Groove 78 may be angled (e.g., 1° to 75° relative to the longitudinal axis L) to facilitate inward movement of the side arm 60, as shown. As the plunger 34 is depressed, the side arm 60 moves inward and compresses the lens component 44 with the wall 61 of the side arm 60 and the interior wall 54 of the bay 42. The side arm 60 moves toward the inner portion 79 of the slider 66 and the raised portion 62 of the side arm 60 mates with the aperture 64 of the cover 53, thereby locking the side arm 60 in place to maintain compression of the lens component 44 (e.g., the elliptical shape). The plunger 34 may then be pushed further so the shaft 70 delivers the lens component 44 through the nozzle 35 and into the patient's eye.

A lumen 80 may be aligned with a deployment channel 82 of the nozzle 35. The deployment channel 82 may receive the lens component 44 from the bay 42 during depression of the plunger 34. The aperture 50 may provide an exit for the deployment channel 82 so that the lens component 44 can be delivered through the nozzle 35 into the eye. The nozzle 35 may be positioned adjacent to the bay 42. In certain embodiments, the nozzle 35 (or a portion thereof) may be integrally formed in or a permanent part of the housing 33 and/or the bay 42.

Figure 8B:
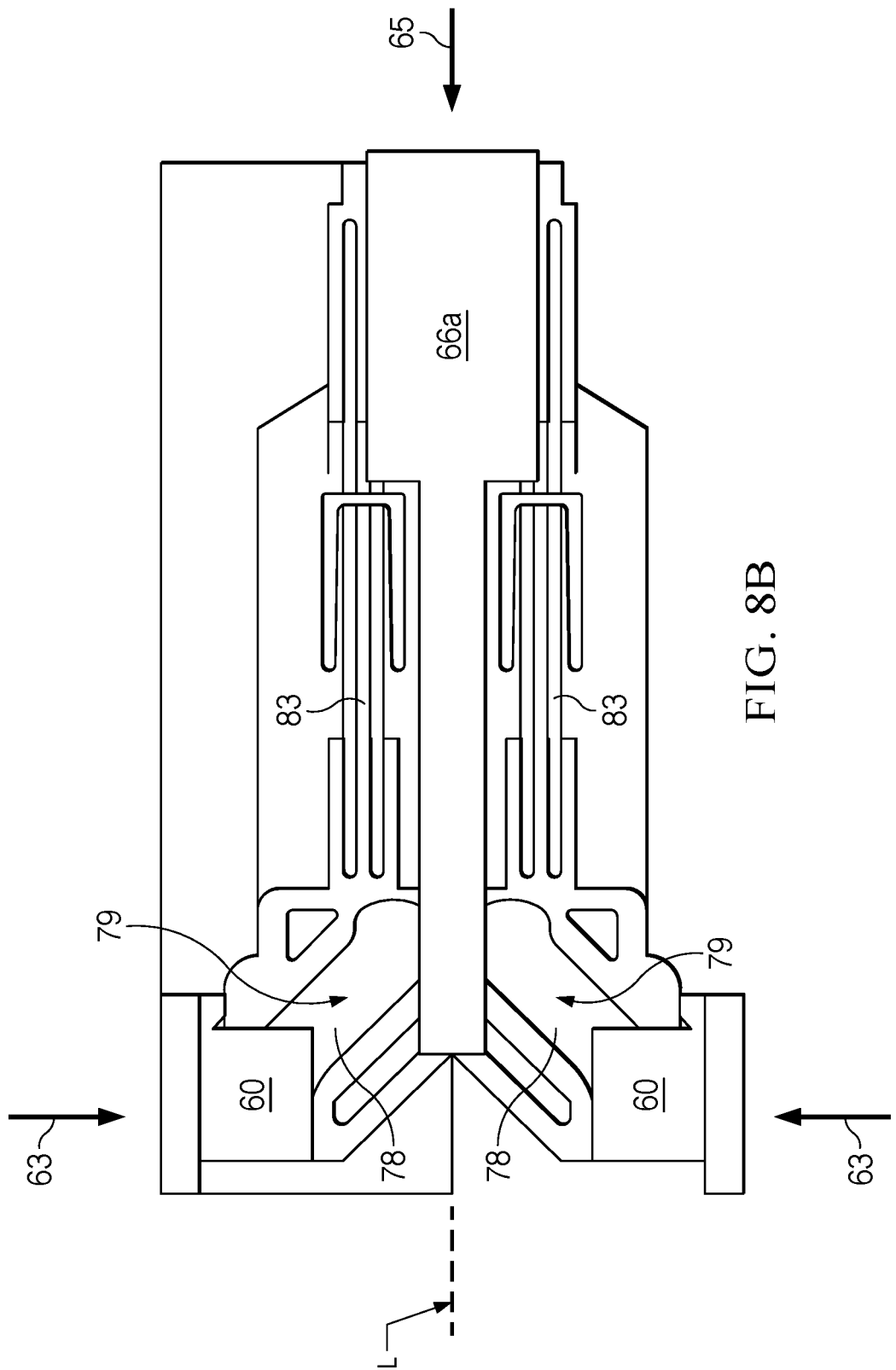
FIG. 8B is a top view of a slider for the dual side arms of FIG. 8A in accordance with embodiments of the present disclosure.

FIG. 8A illustrates another embodiment including an insertion tool 86. The insertion tool 86 may be similar to the insertion tool 32 and/or the insertion tool 85. However, the insertion tool 86 includes two side arms 60. A first side arm 60 may be positioned opposite to a second side arm 60, as shown. Also, a bay 42a may be similar to the bay 42, however, the bay 42a does not include the interior wall 54. Instead, the interior wall 54 is replaced with a second side arm 60 (and accompanying functional features, such as the rails 56, and the portions 58). Upon depression of the plunger 34, both of the side arms 60 move inward (toward each other, as indicated by arrows 63) to compress the lens component 44 due to a slider 66a. The slider 66a may be similar to the slider 66, however, the slider 66a may include multiple tracks 83, multiple grooves 78, and multiple inner portions 79, for example as shown on FIG. 8B.

As the side arms 60 move inward, the shaft 70 moves axially through the channel 52, into the bay 42 to recover the lens component 44 (in a compressed state) from the bay 42. From the bay 42, the shaft 70 delivers the lens component 44 through the intake 48 and out the nozzle 35 via the aperture 50, into the patient's eye.

Axial movement of the slider 66a, the shaft 70 (see arrow 65), and the plunger 34 may be simultaneous with inward movements by the side arms 60. That is, depression of the plunger 34 compresses the lens component 44 and may axially move the lens component 44 through the nozzle 35. The inward movements of the side arms(s) 60 may be perpendicular to the axial movement of the plunger 34 and/or the slider 66a.

In certain embodiments, the walls 61 of the side arms 60 may include protrusions 84 to facilitate compressing of the lens component 44 (e.g., to push the leading haptic extension 18a toward a tucking groove 67 of the nozzle 35), as shown. The tucking groove 67 may be positioned at the intake 48. The tucking groove 67 may be configured to tuck the leading haptic extension 18a during compressing.

In some embodiments, at least one of the side arms 60 may be depressed by a user instead of the user depressing the plunger 34. This may axially pull the plunger 34 and/or the slider 66 (or slider 66a) forward.

In certain embodiments, the insertion tool 32 may be preloaded. That is, when provided to an end-user, the insertion tool 32 may have the lens component 44 (e.g., modular IOL 10, base portion 12, and/or lens portion 14) in an unfolded state already present there within and ready to deliver. Having the insertion tool 32 preloaded with the lens component 44 should reduce the number of steps a user may be required to accomplish before delivering the lens component 44 into a patient's eye. With a reduced number of steps, error and risk associated with delivery of the lens component 44 may be reduced. Further, an amount of time required to deliver the lens component 44 may also be reduced. In some embodiments, the lens component 44 may be pre-loaded into the bay 42.

In an initial position, the lens component 44 may be positioned in the bay 42 prior to the advancement stage. The lens component 44 may be folded (compressed) in the bay 42 as described herein. The lens component 44 may be rolled or folded to reduce a size of the lens component 44. This reduction in size allows delivery of the lens component 44 through a minimally sized incision in the eye.

In the advancement stage, the plunger 34 may advance (via the shaft 70, as shown on FIG. 7A) the lens component 44 from the bay 42 to a dwell position in the deployment channel 82 of the nozzle 35. In some embodiments, the lens component 44 may be folded in the advancement stage. The dwell position may be in the nozzle 35, or may be otherwise situated, for example, in the bay 42.

In the deployment stage, the plunger 34 may advance the lens component 44 from the dwell position and out the aperture 50 of the nozzle 35 into a patient's eye.

An exemplary technique for implantation of the modular IOL 10 into an eye 90 of a patient will now be described with respect to FIGS. 9A-9C.

Figure 9A:
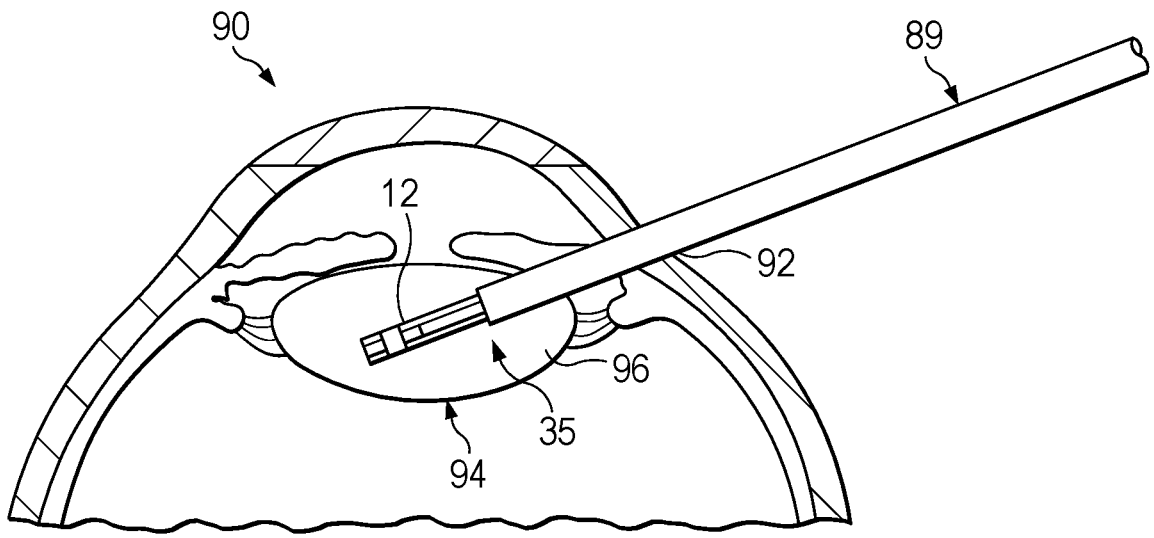
FIGS. 9A-9C illustrate implantation of a modular IOL in accordance with embodiments of the present disclosure.
Figure 9B:
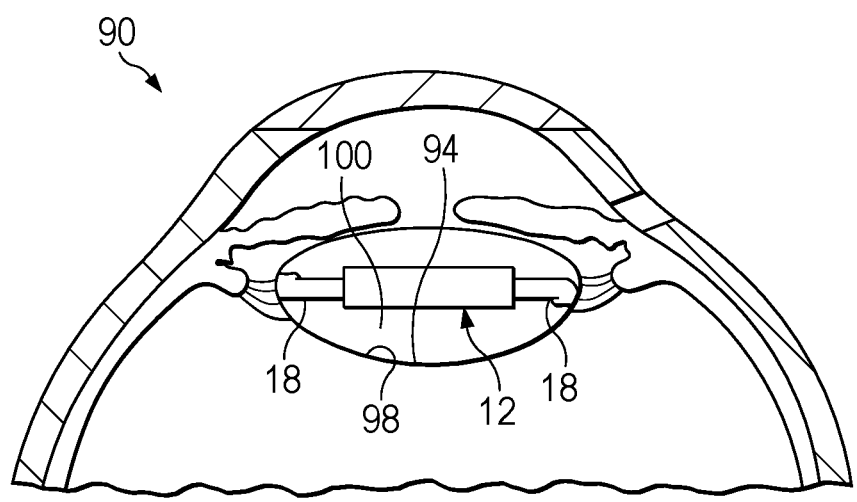

As illustrated on FIG. 9A, an insertion tool 89 (e.g., the insertion tool 32 or the insertion tool 85 or the insertion tool 86) may first dispense the base portion 12 into the eye 90 of a patient. In embodiments, an incision 92 may be made in the eye 90 by a surgeon. For example, the incision 92 may be made through the sclera 94 of the eye 90. The incision 92 may be a suitable width or length. Without limitation, the suitable width and/or length may be less than about 2000 microns (2 millimeters). For example, the incision 92 may have a suitable width and/or length of from about 0 microns to about 500 microns, from about 500 microns to about 1000 microns, from about 1000 microns to about 1500 microns, or from about 1500 microns to about 2000 microns. After the incision 92 is made, the nozzle 35 of the insertion tool 89 may be inserted through the incision 92 into an interior portion 96 of the eye 90. The insertion tool 89 may be actuated to dispense the base portion 12 into a capsular bag 98 of the eye 90. This initial movement of the base portion 12 may be performed at any suitable time, for example, before the incision 92 is made. Once the insertion tool 89 is positioned with the nozzle 35 in the eye 90, the insertion tool 89 may then drive the base portion 12 (in a folded or rolled configuration) through the nozzle 35 and into the interior portion 96 of the eye 90. Upon dispensation, the base portion 12 should unfurl and settle within the capsular bag 98 of the eye 90, as shown on FIG. 9B. The haptic extensions 18 may be manipulated, for example, to engage the inside equator 100 of the capsular bag 98. The haptic extensions 18 may engage the capsular bag 98 to secure the base portion 12 in the capsular bag 98.

Figure 9C:
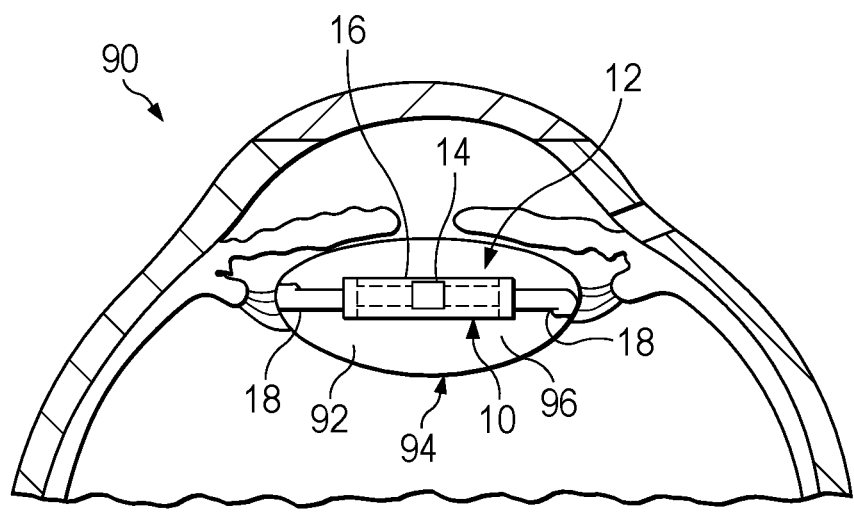

As illustrated on FIG. 9C, the lens portion 14 may be positioned in the interior portion 96 of the eye 90. In the illustrated embodiment, the lens portion 14 is shown positioned in the base 16 of the base portion 12. The lens portion 14 may be delivered in a folded (or rolled configuration) and allowed to unfurl after ejection from the inserter. The lens portion 14 may be positioned in the base 16 of the base portion 12 and secured to the base portion 12, for example, by use of the tabs 30 shown on FIG. 3, to form the modular IOL 10. However, embodiments should not be limited to use of the tabs 30 for interlocking the lens portion 14 and the base portion 12 and other suitable locking mechanisms may be used for securing lens portion 14 to the base portion 12 for forming the modular IOL 10. The base portion 12 may hold the lens portion 14 within the eye 90 so that the lens portion 14 may refract light to be focused on the retina.

Use of the methods and systems described herein may provide numerous benefits and advantages over other IOL delivery systems. For example, the insertion tools including the preloaded IOL, as described herein, improve sterility due to decreased handling by users. Additionally, the insertion tools may allow folding of the IOL and delivery of a folded IOL with a single axial push against a plunger by a user. This reduces a separate folding step. Also, the side arms 60 and the bay 42 include contours that allow for improved folding of the IOL. Further, the cover 53 may include longer and stronger snaps and may be constrained at 3 rather than 2 points for improved stability.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for delivery of a lens component into an eye, comprising:
    a nozzle;
    a bay adjacent to the nozzle, wherein the bay is configured to contain the lens component and comprises a recess in a shape of a haptic extension, wherein the bay comprises an interior wall comprising a slanted surface positioned to contact and fold the lens component;
    a cover that is removably attached to the bay; and
    a cam-actuated mechanism comprising:
        a slider configured to move in a direction toward the nozzle;
        a side arm moveably disposed within the bay, wherein the side arm is positioned at an end of the slider, the end of the slider comprising a groove aligned with the side arm, wherein the groove extends from an outer edge of the slider into an interior portion of the slider, wherein the groove is angled to receive the side arm as the slider moves, and wherein the side arm comprises a slanted wall positioned to contact and fold the lens component, wherein the slanted wall of the side arm is positioned opposite to the interior wall of the bay.

2. The apparatus of claim 1, wherein the bay comprises rails, wherein the side arm is configured to move along the rails as the slider moves toward the nozzle.

3. The apparatus of claim 2, wherein the slider comprises tracks extending in a direction toward the nozzle.

4. The apparatus of claim 3, wherein the tracks of the slider extend in a direction that is perpendicular to the rails of the bay.

5. The apparatus of claim 1, wherein the cover is removably attached to the bay at three stabilization points.

6. The apparatus of claim 5, wherein the side arm comprises a button, wherein the cover comprises an aperture to receive the button to lock the side arm and prevent movement of the side arm.

* * * * *